US008329151B2

(12) United States Patent
Avery et al.

(10) Patent No.: US 8,329,151 B2
(45) Date of Patent: Dec. 11, 2012

(54) HAIR CARE METHOD

(75) Inventors: Andrew Richard Avery, Wirral (GB); Ezat Khoshdel, Wirral (GB); Nerea Ortuoste, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 146 days.

(21) Appl. No.: 12/993,101

(22) PCT Filed: May 20, 2009

(86) PCT No.: PCT/EP2009/056145
§ 371 (c)(1),
(2), (4) Date: Jan. 24, 2011

(87) PCT Pub. No.: WO2009/141381
PCT Pub. Date: Nov. 26, 2009

(65) Prior Publication Data
US 2011/0120488 A1 May 26, 2011

(30) Foreign Application Priority Data
May 21, 2008 (EP) .................................... 08156667

(51) Int. Cl.
*A61Q 5/00* (2006.01)

(52) U.S. Cl. .................................................. 424/70.12
(58) Field of Classification Search .................. None
See application file for complete search history.

(56) References Cited

U.S. PATENT DOCUMENTS 3,519,003 A    7/1970   Mizell ............................. 132/7
3,950,510 A *  4/1976   Adams ....................... 424/70.22

FOREIGN PATENT DOCUMENTS

| EP | 0 951 898   | 10/1999 |
| GB | 1 419 117   | 12/1975 |
| JP | 2004 091399 | 3/2004  |
| JP | 2005 330214 | 12/2005 |
| WO | 2005/105031 | 11/2005 |
| WO | 2007/007291 | 1/2007  |

OTHER PUBLICATIONS

PCT International Search Report in PCT application PCT/EP2009/056145.

* cited by examiner

*Primary Examiner* — Jyothsna Venkat
(74) *Attorney, Agent, or Firm* — Ronald A. Koatz

(57) ABSTRACT

A method of treating hair comprising the step of applying to dry towel dried hair a hair care product comprising a non-surfactant esterified sugar which is non-crystalline at 20° C.

2 Claims, No Drawings

HAIR CARE METHOD

The present invention relates to a composition for improving detangling of hair.

Shampoo and conditioner formulations have been marketed for many years. Despite the prior art there remains the need for compositions which are able to prevent the tangling which occurs during shampooing.

The present invention relates to a method of treating hair comprising the step of applying to dry towel dried hair a hair care product comprising a non-surfactant esterified sugar which is non-crystalline at 20° C.

Also disclosed is the use of a non-surfactant esterified sugar, preferably sucrose acetate isobutyrate to prevent hair from tangling.

The invention has the further advantage that one application of non-surfactant esterified sugar has an effect on cumulative washing. Indeed, cumulative washing can enhance the de-tangling effect.

Preferably the hair is dry.

It is preferred if the method of treating hair comprises the following steps:
  i) applying to the hair a composition comprising a non-surfactant esterified sugar;
  ii) followed by washing the hair.

Compositions of the invention are preferably pre-treatment compositions in that they are applied to dry hair. Shortly after application of the product (within 1 hour, more preferably within 5 minutes) the hair is washed then rinsed.

In the context of this invention towel dried hair can be defined such that 1 g of hair has less than 0.8 g of water, preferably less than 0.6 g associated with it. It should be noted that a dry switch of hair has negligible water associated with it and wet hair greater than 1 g of water associated with it.

Hair is washed in the conventional manner using any commercially available shampoo.

A particularly preferred product for the pre-treatment product is a spray, mousse, gel, serum/oil, cream or lotion. Spray products and/or serums are particularly preferred.

It is preferred if the non-surfactant esterified sugar has a alkyl chain length from C2 to C6. Preferably non-surfactant esterified sugar is a sucrose, particularly preferred is sucrose acetate isobutyrate.

The level of esterified sugar in the tangle prevention composition is preferably from 0.001 to 10 wt % of the total composition, more preferably from 0.01 to 5 wt %.

It is further preferred if the level of non-surfactant esterified sugar in the composition is such that it delivers from 0.3 to 12 mg of sugar per g of hair, preferably from 0.6 to 6 mg, more preferably from 1 to 1.5 mg.

The composition may comprise a solvent for the non-surfactant esterified sugar. Suitable solvents include ethanol, isopropyl alcohol, n-propyl alcohol, n-butyl alcohol isobutyl alcohol, caprylic/capric triglycerides or mixtures thereof. Water may also be present with these solvents. Particularly preferred is ethanol, of particular benefit is an ethanol and water mix.

It is preferred if the weight ratio of non-surfactant esterified sugar to solvent is from 0.01:100 to 1:100.

Compositions of the invention may further comprise a silicone, more preferably in the form of an emulsion.

In some instances, particularly when the product is a serum or oil the composition may comprise cyclopentasiloxane (D5). Also preferred for oils serums are triglycerides.

Amino-functional polydimethyl siloxanes which have the CTFA designation amodimethicone may be used with the present invention. Preferred silicones are emulsions and include silicones such as polydiorganosiloxanes, in particular polydimethylsiloxanes which have the CTFA designation dimethicone, polydimethyl siloxanes having hydroxyl end groups which have the CTFA designation dimethiconol.

Suitable silicone emulsions for use in compositions of the invention are available from suppliers of silicones such as Dow Corning and Momentive. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol.

Suitable amodimethicone emulsions are DC939, DC7134 (from Dow Corning) and SME253 (from Momentive).

Silicone will generally be present in a composition of the invention at levels of from 0.05 to 20%, preferably 1 to 15%, more preferably from 2 to 10% by total weight of silicone based on the total weight of the composition.

In instances where the product is a serum or oil the level of solvent is higher than that stated above, in these cases it is usually from 80 to 99 wt % of the total weight of the composition.

The Examples will now be illustrated with reference to the following non-limiting Examples. Inventions according to the invention are demonstrated by a number, comparative inventions are demonstrated by a letter.

EXAMPLES

| Example 1 | Wt % |
| --- | --- |
| Sucrose acetate isobutyrate | 0.2 |
| Ethanol | 50 |
| Minors and Water | to 100 |

Detangling Experiment

Two sets of switches were tested to evaluate the ability of sucrose acetate isobutyrate (SAIB) deposits to reduce the amount of energy required to detangle hair. The first set was treated as described below using only Dove Intensive Care Shampoo (European formulation 2007). The second set was treated with Example formulation 1 as a pre treatment before applying Dove Intensive Care Shampoo.

In each case, dark brown European hair switches of mass 2.5 g and length 6" were used without any deliberate mechanical or chemical modification. Each switch was subject to multiple treatment cycles defined as follows: if used, Example formulation 1 was applied to the dry hair switch. 1.5 ml of this solution was syringed into the hair switch and evenly distributed. Dove Intensive Care shampoo was then applied; 0.5 g per switch, 1" from the clamped end and worked into the switch using a controlled tangling instrument.

The switch was then rinsed to remove the shampoo and placed into the detangling apparatus. This comprised an Instron load frame with a 1 kN load cell. A narrow, grey Dupont Starflite comb, no. 858 was used for each switch at a fixed speed of 4 cm/s. The comb was inserted 1" from the bottom of the switch and combed through. The comb was then repeatedly combed through starting from positions 1" further up the switch each time until a distance of 5" from the bottom was reached. If at any pass, the load cut off of 30 N was reached, that pass would be repeated. The energy per pass was calculated by the software and all 5 values added together for each test. This value was recorded as the detangling energy.

Once the switch had been fully detangled the whole wash, tangling and detangling cycle was repeated. Ten cycles were performed for each switch. Three replicates were used for each formulation.

The process was repeated up to 8 times.

The results are as follows:

|  | 1X | 2X | 3x | 4x | 5x | 6x | 7x | 8x |
|---|---|---|---|---|---|---|---|---|
| Dove Shampoo Example A | 0.38 | 0.26 | 0.39 | 0.40 | 0.33 | 0.40 | 0.35 | 0.49 |
| Example 1 followed by Dove Shampoo | 0.29 | 0.24 | 0.28 | 0.24 | 0.24 | 0.25 | 0.22 | 0.26 |

These results show that application on hair of a pre-treatment product comprising sucrose acetate isobutyrate prevents the hair from tangling. Furthermore after initial application on repeat washing the effect remains, with the Example of the invention, this is not the case for the comparative example.

The following Examples (a cream formulation) show the benefit of using a non-surfactant esterified sugar compared with a surfactant based sugar.

| INCI Name | Supplier | % active in raw material | Comparative example B | Invention Example 2 |
|---|---|---|---|---|
| dimethicone and amodimethicone | Dow Corning | 70 | 2.69 | 2.69 |
| glycerol | BDH | 100 | 1.60 | 1.60 |
| behenyl alcohol | Cognis | 100 | 2.00 | 2.00 |
| stearamidopropyl dimethylamine | Inolex | 100 | 0.80 | 0.80 |
| hydroxyethyl cellulose | Aqualon | 100 | 0.24 | 0.24 |
| lactic acid | Purac | 88 | 0.16 | 0.16 |
| sucrose acetate isobutyrate (SAIB) and ethanol | Eastman | 90 | 0.00 | 0.33 |
| mineral oil | Silkolene | 100 | 4.50 | 4.50 |
| sucrose hexaerucate | Mistubishi Kagaku | 100 | 0.30 | 0.00 |
| water and minors |  | 100 | To 100 | To 100 |
| Votes |  |  | 39 | 60 |

Virgin Dark Brown European (7 g, 10 inch) Hair switches treated with the examples (dry application followed by repeatedly washing 6 times with a basic, non-conditioning shampoo) were assessed for ease of combing by a trained panel. Ease of comb data analysed by Bradley Terry test shows a highly significant win for the Example of the invention Example 2 comprising SAIB (easier) with p=0.005

Example of Serum Type Formulation

| Chemical Name | % in raw material | % w/w Example 3 water in oil serum |
|---|---|---|
| alpha, omega dihydroxylated polydimethylsiloxane/ polydimethylsiloxane | 12 | 23.10 |
| hydroxyethyl cellulose | 100 | 0.21 |
| PEG-400 | 100 | 3.50 |
| Propylene glycol | 100 | 41.57 |
| Sodium Chloride | 100 | 1.40 |
| Polyacrylamide and C13-14 isoparaffin and laureth-7 | 47 | 6.00 |
| Sodium Benzoate | 100 | 0.70 |
| Sucrose acetate isobutyrate and caprylic and capric triglycerides | 80 | 0.90 |
| water | 100 | 22.62 |

The invention claimed is:

1. A method of detangling hair comprising the step of applying to dried hair a pretreated hair care product comprising
   1. 0.01 to 5 wt % of sucrose acetate isobutyrate
   2. 0.05 to 20 wt % of silicone
   3. Glycerol
   4. Behenyl alcohol
   5. Stearamidopropyl dimethylamine
   6. Hydroxyethyl cellulose
   7. Lactic acid
   8. Ethanol
   9. Mineral oil
   10. Water, wherein the pretreatment hair care product is in the form of a cream.

2. A method of detangling hair comprising the following steps:
   i) applying to the hair a pretreatment hair product according to claim 1;
   ii) followed by washing the hair.

* * * * *